(12) United States Patent
Christ et al.

(10) Patent No.: US 6,730,026 B2
(45) Date of Patent: May 4, 2004

(54) MEDICAL SYSTEM FOR MONITORING A MEASURED VALUE OF A PATIENT RELATING TO BLOOD-CLOTTING

(75) Inventors: Tilo Christ, Erlangen (DE); Arne Hengerer, Erlangen (DE); Volker Schmidt, Erlangen (DE); Werner Striebel, Schwarzenbruck (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/056,409

(22) Filed: Jan. 25, 2002

(65) Prior Publication Data

US 2002/0099283 A1 Jul. 25, 2002

(30) Foreign Application Priority Data

Jan. 25, 2001 (DE) .......................... 101 03 330

(51) Int. Cl.[7] .............................. A61B 5/00; G06F 17/00
(52) U.S. Cl. ........................ 600/300; 600/369; 128/920
(58) Field of Search ................................. 600/300, 301, 600/369, 576, 587, 368; 340/573.1; 128/903, 904, 920, 925; 705/2–4; 707/1, 104

(56) References Cited

U.S. PATENT DOCUMENTS

| 5,517,405 A | 5/1996 | McAndrew et al. |
| 5,544,661 A | 8/1996 | Davis et al. |
| 5,630,209 A | 5/1997 | Wizgall et al. |
| 5,967,975 A | 10/1999 | Ridgeway |
| 5,971,931 A | 10/1999 | Raff |
| 6,024,699 A | * 2/2000 | Surwit et al. ............... 600/300 |
| 6,154,750 A | * 11/2000 | Roberge et al. ............ 707/104 |
| 6,171,237 B1 | * 1/2001 | Avitall et al. .............. 600/300 |
| 6,294,999 B1 | * 9/2001 | Yarin et al. ............. 340/573.1 |
| 6,402,704 B1 | * 6/2002 | McMorrow ................ 600/576 |

FOREIGN PATENT DOCUMENTS

| EP | 1 101 437 | 5/2001 |
| WO | WO 93/01574 | 1/1993 |
| WO | WO 98/35326 | 8/1998 |
| WO | WO 00/32101 | 6/2000 |
| WO | WO 01/50950 | 7/2001 |

* cited by examiner

*Primary Examiner*—Eric F. Winakur
*Assistant Examiner*—Michael Astorino
(74) *Attorney, Agent, or Firm*—Schiff Hardin LLP

(57) ABSTRACT

A medical system for monitoring a measured value of a patient characterizing blood clotting and/or for setting a medication that influences blood clotting for a patient in a home environment, has a device for acquiring measured values of the patient relating to blood clotting, a device for transmitting the measured values to a system central, a device for interrogating the measured values, and a reception device at a monitoring person. The system central has a memory for the measured values, an analysis device for the measured values by comparing the measured values to stored reference values, an alarm generator which generates an alarm signal upon a recognition of predetermined conditions, and a routing device for forwarding the alarm signal to a reception device of a person to be alerted in a process chain.

11 Claims, 3 Drawing Sheets

MEDICAL SYSTEM FOR MONITORING A MEASURED VALUE OF A PATIENT RELATING TO BLOOD-CLOTTING

BACKGROUND OF THE INVENTION

1. Field of the Invention

The present invention is directed to a medical system for monitoring a measured value of a patient characterizing blood clotting of the patient and/or for setting a medication that influences the blood clotting for a patient in a home environment.

2. Description of the Prior Art

The frequency of cardiovascular conditions in the population is steadily increasing. When suffering from such conditions, for example cardiac infarctions, patients often must live with bypasses, artificial heart valves or artificial blood vessels. Accompanying this is the constant risk of recurrent thromboses, embolisms or disturbances of the heart rhythm, for example, for which patients usually must be treated life-long with medications that influence blood clotting, known as anticoagulants, such as Marcumar, Falithrom or Warfarin. This therapy is highly effective in and of itself but some physicians are wary about prescribing such medications because the medication level is relatively difficult to set. The effect of the medications is decisively dependent on the nutritional habits of the patient as well as on the taking of further medications. Whereas an overdosage creates the risk of life-threatening hemorrhages, for example renal hemorrhage or massive cerebral hemorrhage, thromboses, infarctions or strokes cannot be precluded in the case of an under-dosing.

The monitoring of a measured value of a patient characterizing blood clotting as well as the setting of a medication that influences blood clotting for a patient in an extra-clinical environment heretofore has been only inadequately addressed. There are known coagulation measuring instruments with which the patient can measure coagulation values at home, these values then being reported to the attending physician, for example on paper or as a telefax. However, close cooperation with a physician is required for an adequate treatment, particularly for monitoring the activity of the patient, during a readjustment or change of medications, the administration of additional medications or for acute emergency situations.

SUMMARY OF THE INVENTION

An object of the present invention is to provide a medical system of the type initially described wherein extra-clinical monitoring of a value of a patient characteristic for coagulation and/or an extra-clinical setting of a medication influencing coagulation for a patient can ensue a degree of medical care that is necessary for the good health of a patient.

According to the invention, this object is achieved in a medical system for monitoring a measured value of a patient characterizing blood clotting and/or for setting a medication that influences blood clotting for a patient in a home environment having a device for acquiring measured values of the patient relating to blood clotting, a device for the transmission of the measured values to a system central, having a device for interrogating the measured values and a reception device at a monitoring person. The system central has a memory for the measured values, an analysis device for the measured values for comparing the measured values to stored rated values, an alarm generator for generating an alarm signal and a routing device for forwarding the alarm signal to a person to be alerted in a process chain. With this system, the monitoring of measured values relating to the blood clotting of a patient can be segregated out of the clinical area or from a physician's practice and relocated into the living environment of the patient. In particular, the system monitors three quantities: the patient compliance, the measured values of the patient relating to the coagulation and the physician compliance. For a comprehensive medical care of the patient, alarms thus can be triggered if the patient does not generate and communicate measured values or does so too often, when the measured values lie in a health-jeopardizing range, so that an emergency situation is impending or has already occurred, and if the alerted location does not react adequately.

Immediate measures required in the event of sickness can be initiated without delay in an embodiment wherein the alarm generator is fashioned such that it generates an alarm signal given upward or downward transgression, particularly given a significant upward or downward transgression, of stored reference value limits by the measured values. The alarm signal is routed to a reception device or a person in a treatment chain or a person in an emergency chain.

In a version of the invention, the alarm generator can generate an alarm signal if measured values fail to arrive, this alarm signal being routed to a reception device of the patient, and/or it can generate an alarm signal given lack of a reaction of a person in the treatment chain to specifically identified measured values that have been routed to a reception device of the emergency chain.

It is advantageous for the routing device to route the alarm signal to a predetermined, selectable reception device of the process chain or to route the alarm signal automatically to a reception device of the process chain defined by the routing device, taking availability into consideration.

A fast and effective notification in case of emergency can be achieved in an embodiment wherein the routing device is a learning expert system that effects the alerting of the process chain, for example notification of the family physician, calling the emergency physician, organizing the transport service and/or preparing the clinic.

Undesired false alarms are reduced or precluded in an embodiment wherein the analysis device is a learning expert system that interprets the measured values disease-specifically and/or problem-specifically on the basis of rule systems or based on probabilities, as a result of which the alarm signal is triggered.

In a version of the invention provides that the alarm generator generates different alarm signals dependent on the urgency of a reaction to an event, these alarm signals being routed to reception devices of a treatment and/or emergency chain.

DESCRIPTION OF THE PREFERRED EMBODIMENTS

Figure 1:
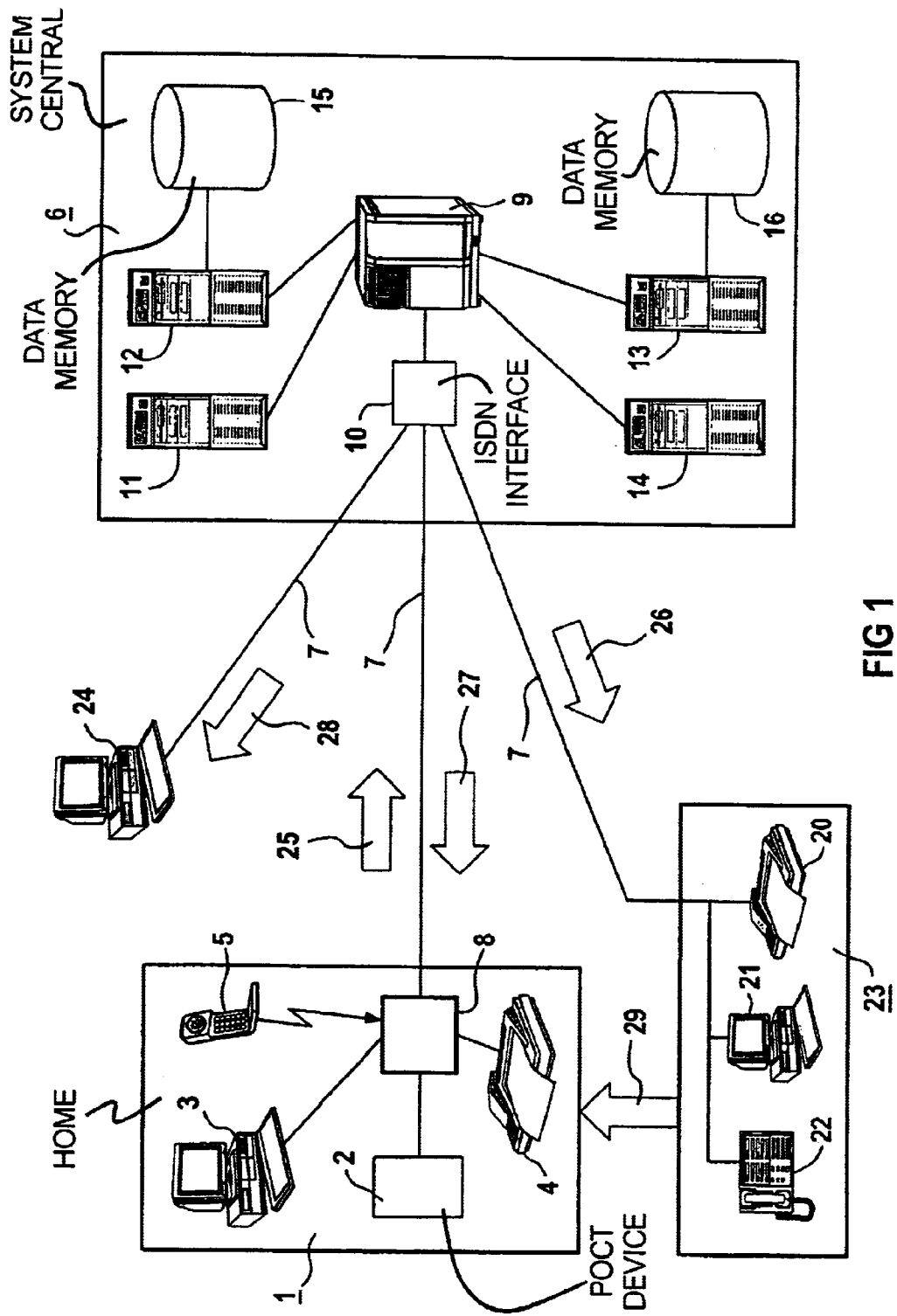
FIG. 1 schematically illustrates an inventive medical system for monitoring a measured value of a patient characteristic of blood clotting and for setting a medication for a patient that influences blood clotting.

FIG. 1 shows an inventive system for monitoring measured values of a patient (not shown) relating to blood clotting and for setting a medication for the patient at home 1 that influences blood clotting. The acquisition of the measured values, which characterizes the blood clotting of the patient and includes information about the type, dose and taking of medications influencing the blood clotting as well as information about food consumed or color of urine, ensues partly automatically and partly manually by the patient or a care giver. A POCT device 2 (point of care testing), also called a coagulation monitor, is employed for this purpose. This device 2 makes it possible to identify coagulation values such as Quick or PTT of the patient and also makes it possible to undertake a self-test and a self-dosage of a medication, for example Warfarin. Such POCT devices are distributed, for example, by November AG under the name Novi Quick or by Roche under the name Coagucheck or Coagucheck Plus. The information relating to the eating habits and the color of urine, in contrast, can be acquired in a questionnaire.

The bundle 25 of measured values, preferably acquired at regular points in time, after corresponding input or measurement, can be communicated to a system center 6 directly from the device 2 or via a transmission device for information, for example by personal computer 3, by fax machine 4 or by telephone or cell phone 5, that is connected to the device 2. This can ensue via a communication network, for example via an ISDN network 7, to which the corresponding terminal devices are connected via an ISDN interface 8. Insofar as they are Internet-compatible, however, the terminal devices also can be connected to the Internet for the data transfer via a corresponding interface, the ISDN interface 8 also being suitable for this purpose.

The system center 6 serves the purpose of accepting and storing the measured values, and preferably further-processes the measured values and, when necessary, a triggers alarm signals.

To this end, a gateway 9 that is connected to the ISDN network 7 via an ISDN interface 10 is provided in the system center 6. An Internet proxy server 11 for access to the Internet, an analysis device 12 for the measured values, a patient data server 13 for administering the patient data and a communication server 14 operating as routing device for the collaboration of all components and for routing information, can be connected to the gateway 9. A data memory 15 for the measured values is connected to the analysis device 12 and a data bank 16 as memory device is connected to the patient data server 13.

The measured values are accepted in the system center 6 via the ISDN interface 10 and are stored long-term in the data memory 15. The analysis device 12 has a comparator for comparing the measured values to reference values stored in the data memory 15 and interprets the point in time of the transmission of the measured values. The analysis device 24 also has an alarm generator for generating messages and alarms given abnormal measured values, given the failure of measured values to arrive from the patient and given a lack of a reaction on the part of a physician or a patient to an alarm.

All information required for activating the alarm generator and for realizing a forwarding of alarms and messages given the absence of the intended recipient thus is merged in the system center 6.

Reception devices such as, for example, a fax machine 20, a personal computer 21, a telephone 22 or cell phone are connected to the system center 6. These can belong, for example, to a standby physician and, for example, are arranged in a cooperative practice 23 of physicians.

In the exemplary embodiment, further, a personal computer 24 of a practice of a primary physician is connected via the ISDN network 7 to the gateway 9 of the system center 6. An output of the measured values stored in the data memory 15 to one of the terminal devices for physicians ensues via the ISDN interface 10.

When the acquisition of the bundle 25 of measured values is carried out by a care giver, then a personal digital assistant (PDA) or a laptop is provided for this person, all patient data of patients visited by this care service are entered into that device. Synchronization of the data can ensue immediately, for example via a cell phone/Internet connection, or can ensue at a later point in time when the care giver returns to the office or to the practice.

As already indicated one or more alarms is triggered by the alarm generator of the analysis device 12, preferably given the presence of one of the event constellations such as the failure of measured values to arrive from a patient, the presence of abnormal measured values or the lack of a reaction on the part of the informed person to a generated alarm, either a physician or the patient himself. The analysis device 12 thereby determines whether measured values or measured value constellations are to be classified as a health risk. Limits from the literature or medication-specific limits are used as a criterion, these being stored in the data memory 15. Further, the attending physician can define individual limits for the patient.

An alarm 27 to the patient is triggered, for example, when measured values that have become due from the patient are not supplied. Further, an alarm 26 is routed to the terminal devices 20 through 22 of the cooperative practice 23 or to the primary physician due to transgression of a limit value, preferably a downward or upward transgression of reference value limits, by the measured values. In the practice, every treating physician who has authorization can fetch the measured values stored in the data memory 15 with a personal computer, a telephone, a fax, a cell phone or some other communication device.

An expert system that interprets the measured values in a manner disease-related to a pathology specifically and specifically related to a particular problem on the basis of rule systems or interprets the measured values based on probabilities can be used for reviewing the measured values and triggering alarms. A customization of the expert system to the patient is thereby achieved, i.e. the expert system learns the patient, and the coagulation values of the patient and becomes more and more familiar with the physical values related thereto during the course of the monitoring process. As a learning system, it constantly makes predictions about future measured values to be anticipated and compares these to the actual measured values. An individualized monitoring is thus realized.

In the case of complex alarms, an expert system can be utilized that assumes tasks of the process chain such as reminding the patient, notifying the family physician, calling the emergency physician, organizing the transport service and/or readying the clinic, taking the availability of the alarm recipient into consideration.

The process chain thereby includes the totality of participating persons and institutions. These include the patient, the treatment chain with physician, care and transport service as well as the emergency chain with fire department router, emergency and transport services as well as the hospital.

Alarms can be generated with different urgency levels such as, for example, utmost urgency, urgent, routine or standard dependent on the urgency of a reaction of a notified person or institution. Which measured values lead to which urgency levels can be defined with the same mechanisms as the evaluation of the measured values and can be stored in the data memory 15.

Figure 2:
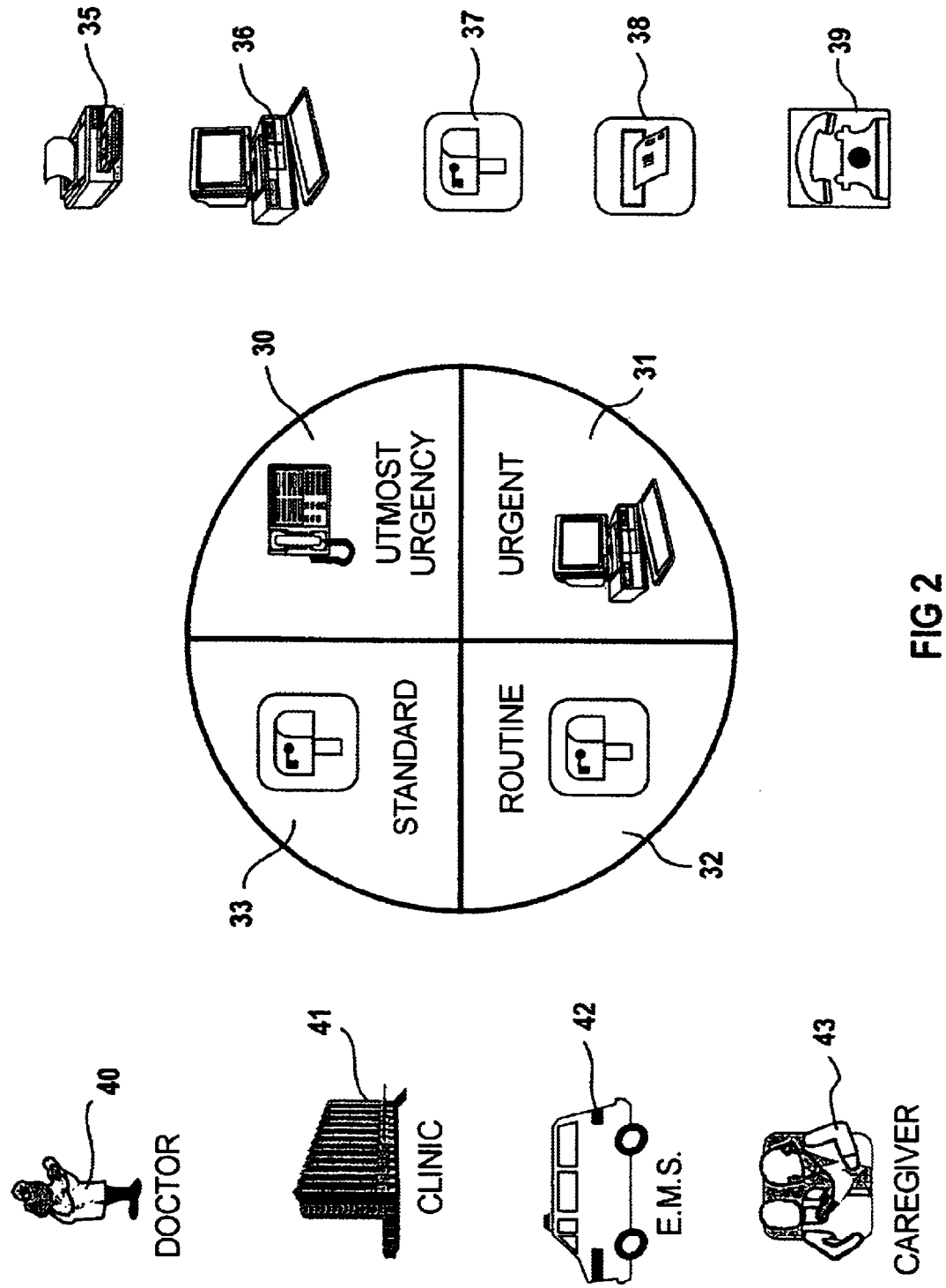
FIG. 2 illustrates a user interface for configuring a central alarm generator in accordance with the invention.

The user carries out the configuration of the central alarm generator of the cooperative practice 23. The monitoring entity, such as one of the physicians, personally defines how he or she wishes to receive messages having different urgency. The user interface shown in FIG. 2 is employed for this purpose. The communication circle is divided into segments 30 through 33 that represent the urgency levels of the alarm messages.

For configuration, the physician drags the device icons from the series of communication devices 35 through 39 of the user into the corresponding segments 30 through 33, namely those communication devices via which the physician would like to be reached given the arrival of a classified message. The configuration is stored in the system center 6.

Given the selected configuration according to FIG. 2, the physician is informed by telephone 22 in cases of utmost urgency, by e-mail via the personal computer 21 given urgent cases and by mail in all other instances.

If a physician does not react to an alarm within a reasonable time, the alarm generator of the analysis device 12 forwards the alarm to the system center 6. The configuration regarding the person to whom the alarm signal should be routed is undertaken by the physician personally. To this end, the physician employs a communication circle shown in FIG. 3 that is segmented on the basis of the urgency levels. The physician drags the respective icons representing physicians and/or institutions 40 through 43 that are to be alerted in an emergency when the physician himself does not react into the corresponding circle segments.

Figure 3:
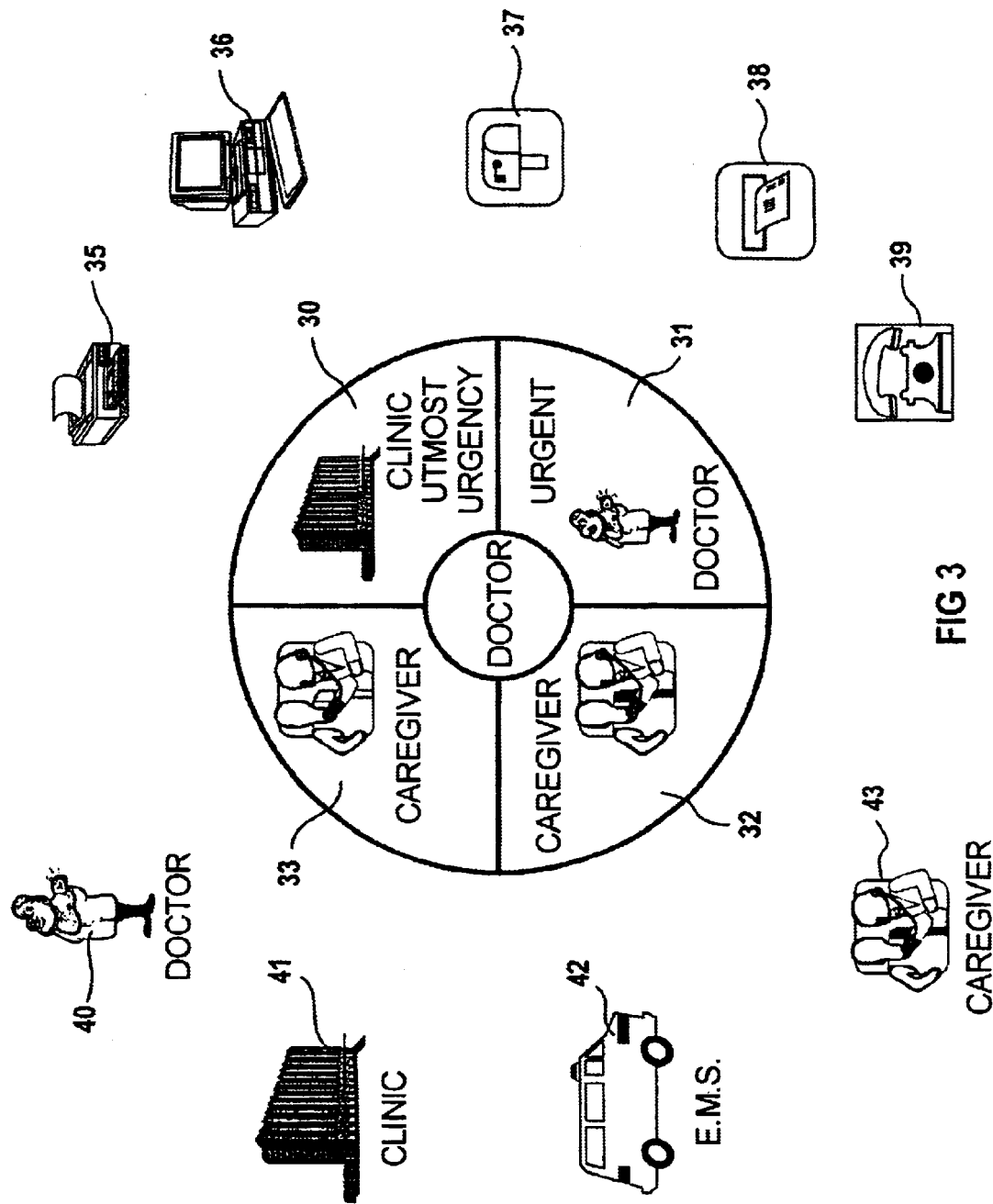
FIG. 3 illustrates a user interface for configuring the forwarding of alarms in accordance with the invention.

Given the selected configuration according to FIG. 3, a clinic 41 is notified given cases of utmost urgency, a different, selected physician 40 is notified given urgent cases, and the care service is notified in all other cases.

Alternatively, the alerting of the physician and the forwarding, if necessary, ensue in a single communication circle.

Default settings can be prescribed by the server, so that the physician is presented with a meaningful proposal given an initial installation, with a preference list of the physician being taken into consideration.

Further, alarms with different complexity can be generated. In the simplest case, only the physician or the physician's representative are informed. The alarms, however, can be forwarded pathology-specifically to different locations. Thus, the alarms relating to the medication setting can be forwarded to an attending specialist and acute emergencies as a result of coagulation values deviating greatly from the norm can be forwarded to a clinical establishment. The alarms initiate measures that are additionally required. For example, they alert the attending physician when internal hemorrhaging is suspected and simultaneously alert the Emergency Response routing center and the transport service of the emergency chain.

The information channel to the patient also can be configured so that the patient also can receive messages from the physician. To that end, the patient can likewise configure a communication circle into which the patient enters the paths by which the patient can be reached.

Alternatively, the patient can set a forwarding of urgent messages when on vacation or when in the hospital.

The sending of information occurs such that the analysis device 12 generates a message and forwards it to the communication server 14 for the sending of the message. The communication server 14, as a routing device, sends messages to a recipient using a telephone book sub-routine wherein contact information about an addressable recipient are offered.

The physicians' terminal device serve the purpose of reproducing and presenting the measured values as well as the parameterization of the alarm generator, the communication paths for sending messages and the terminal devices for patient and/or care giver.

An alarm audio devices emits the messages sent by the message transmission at the recipient. Specific embodiment of the terminal devices for patient and/or care givers can serve this purpose, for instance a PDA with modem, a telephone with voice or dual tone multi-frequency signaling (DTMF), a measuring instrument with integrated modem, a TV set-top box, a cell phone, a WWW form, or a paper form and a WWW form.

The system center 6 has an interface for coupling to a quality assurance system in order to obtain a result quality under real conditions. Further, the central system 6 can comprise an interface for coupling to an accounting module.

In various embodiments the alarm generator can trigger an alarm given incorrectly acquired measured values, trigger an alarm given compliance problems on the part of the patient, trigger an alarm when the reaction time of the physician to urgent messages is too long, and forward an alarm if the physician does not react.

Messages can, for example, be communicated via voice by telephone, or by SMS, e-mail, WWW, WAP, telefax, proprietary service or letter mail.

The analysis device 12 for the measured values and the patient data server 13 can be implemented for data collecting such that the measured values are stored dependably and in pseudonym form.

The terminal devices for physicians preferably include a graphic user interface based on Internet technologies. For parameterizing the alarm generator, the device offers the method visualized in FIG. 2. The method illustrated on the basis of FIG. 3 serves the purpose of parameterizing the notification paths.

Dependent on the alarm level, the alarm terminal device can, for example, be a telephone, cell phone, e-mail terminal, WWW terminal, fax machine, a terminal for using a proprietary service or a conventional postal service mailbox.

The alarm terminal device in the cooperative practice 23 can have a return channel 29 for transmitting therapy instructions to the patient and/or care giver, so that a therapy can be implemented despite the spatial separation between physician and patient (tele-therapy).

The inventive system creates a "virtual" care station at the patient's home that includes a central alarm generator system that generates alarms given:

Faulty patient compliance (anticipated measured values of the patient fail to arrive)

Upper transgression of thresholds (i.e. the measured values lies in an abnormal range).

Faulty physician compliance (anticipated reaction to the alarm on the part of the physician fails to occur).

The inventive configuration capability for contacting and alarm forwarding allows customized settings according to the current requirements of each treatment case.

Back-up procedures ensure a forwarding given the lack of a reaction on the part of a physician.

Disease-specific alarm forwardings can be set.

A treatment chain such as emergency physician, transport, clinic, care service and/or Reha can be notified and coordinates.

A customized configuration of the data communication of physician and/or care giver to the patient can be selected by the patient.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical system for monitoring a measured value of a patient in a home environment, characterizing blood clotting of said patient, comprising:

a measured value acquisition device adapted for interaction with a patient to acquire measured values relating to blood clotting of said patient;

a transmission device connected to said measured value acquisition device for transmitting said measured values to a system central;

said system central having a memory at which reference values are stored, and an analysis device, supplied with said measured values and having access to said memory, for comparing the measured values to said reference values and which identifies a level of urgency, from among a plurality of different levels of urgency, for any treatment needed by the patient dependent on a relationship of said measured values to said reference values, and an alarm generator which generates at least one alarm signal from among a plurality of different alarm signals respectively allocated to said different levels of urgency;

a plurality of reception devices located remote from said system central, and respectively associated with different persons, respectively adapted o respond to said different levels of urgency, in a response chain; and said system central further including a routing device supplied with said alarm signal, and said routing device routing said alarm signal to at least one of said reception devices to notify at least one person in said response chain adapted to the level of urgency identified by said analysis device, said routing system automatically differently routing said alarm signal, dependent on the level of urgency, to respectively different persons in said response chain.

2. A medical system as claimed in claim 1 wherein said memory at said system central contains stored reference value limits associated with said reference values, and wherein said alarm generator generates said alarm signal given upward or downward transgression of said stored reference value limits by said measured values, and wherein said routing device routes said alarm signal to a reception device, among said plurality of reception devices, associated with a person responsible for treatment of said patient.

3. A medical system as claimed in claim 1 wherein said memory at said system central contains stored reference value limits, associated with said reference values, and wherein said alarm generator generates said alarm signal given significant upward or downward transgression of said reference value limits by said measured values, and wherein said routing device routes said alarm signal to a reception device, among said plurality of reception devices, associated with an emergency response person.

4. A medical system as claimed in claim 1 wherein said alarm generator generates said alarm signal given failure of said measured values to arrive at said system central, and wherein said routing device routes said alarm signal to a reception device, among said plurality of reception devices, associated with said patient.

5. A medical system as claimed in claim 1 wherein said analysis unit generates an analysis result dependent on the comparison of said measured values to said reference values, and wherein said routing unit routes said analysis result to a reception device, among said plurality of reception devices, associated with a person responsible for treatment of said patient, and wherein said alarm generator generates said alarm signal given a lack of reaction of said person responsible for treatment of said patient, and wherein said routing unit routes said alarm signal to a further reception device, among said plurality of reception devices, associated with an Emergency Response person.

6. A medical system as claimed in claim 1 wherein said alarm generator generates said alarm signal with routing information contained therein, and wherein said routing device routes said alarm signal to one of said plurality of reception devices designated by said routing information.

7. A medical system as claimed in claim 1 wherein said routing device automatically routes said alarm signal to one of said reception devices defined by said routing device dependent on availability.

8. A medical system as claimed in claim 1 wherein said routing device is a learning expert system.

9. A medical system as claimed in claim 1 wherein said analysis device comprises a learning expert system that interprets said measured values in a pathology specific manner using an analysis basis selected from the group consisting of rule systems and probabilities.

10. A medical system as claimed in claim 1 wherein said analysis device comprises a learning expert system that interprets said measured values in a problem specific manner using an analysis basis selected from the group consisting of rule systems and probabilities.

11. A medical system as claimed in claim 1 wherein said analysis device comprises a learning expert system that interprets said measured values in a pathology specific and a problem specific manner using an analysis basis selected from the group consisting of rule systems and probabilities.

* * * * *